United States Patent

Wurtman

[11] 4,224,343
[45] Sep. 23, 1980

[54] PROCESS AND COMPOSITION FOR DECREASING BLOOD SERUM PROLACTIN LEVELS

[75] Inventor: Richard J. Wurtman, Waban, Mass.

[73] Assignee: Massachusetts Institute of Technology, Cambridge, Mass.

[21] Appl. No.: 27,533

[22] Filed: Apr. 5, 1979

Related U.S. Application Data

[63] Continuation-in-part of Ser. No. 898,740, Apr. 24, 1978.

[51] Int. Cl.$^2$ ............................................. A61K 31/195
[52] U.S. Cl. ................................................... 424/319
[58] Field of Search ........................................ 424/319

[56] References Cited
PUBLICATIONS

Chem. Abstr., 79-87422s (1973), Goldstein.
Chem. Abstr., 85-14103c (1976), Sedvall.

Primary Examiner—Stanley J. Friedman
Attorney, Agent, or Firm—Arthur A. Smith, Jr.; Paul J. Cook

[57] ABSTRACT

The level of prolactin in blood serum is reduced by administering tyrosine to a human. The tyrosine can be administered alone, or concomitantly with a drug which tends to increase blood serum prolactin levels.

4 Claims, 2 Drawing Figures

PROCESS AND COMPOSITION FOR DECREASING BLOOD SERUM PROLACTIN LEVELS

The Government has rights in this invention pursuant to Grant No. AM-14228 awarded by the National Institute of Health.

REFERENCE TO RELATED APPLICATIONS

This application is a continuation-in-part of application Ser. No. 898,740, filed Apr. 24, 1978.

BACKGROUND OF THE INVENTION

This invention relates to a method and composition for decreasing blood serum prolactin levels.

It is well known that the neurotransmitters dopamine and norepinephrine are derived from dihydroxyphenylalanine (DOPA). DOPA is, in turn, produced in neurons by the enzymatic hydroxylation of the amino acid tyrosine. This process is catalyzed by the enzyme tyrosine hydroxylase. The DOPA is decarboxylated to dopamine by the enzyme aromatic L-amino acid decarboxylase (AAAD) and norepinephrine is produced from dopamine in neurons that also contain the enzyme dopamine beta-hydroxyase. It is also known that within this reaction chain, the rate-limiting step is the conversion of tyrosine to DOPA. For this reason, DOPA has been administered to patients who suffer medical disability resulting from dopamine deficiency in diseases such as Parkinson's Disease. Unfortunately, DOPA, when administered, is taken up by cells throughout the body and converted to dopamine and this interferes with the normal metabolic processes in these other cells. In addition, DOPA interferes with the body's normal storage of the neurotransmitter serotonin, and lowers brain levels of the compound S-adenosylmethionine. It is believed that these effects contribute to such unwanted side-effects as the "On-Off Phenomenon" and, in some patients, psychotic symptoms. Other types of drugs that act by increasing dopamine and norepinephrine levels in synapses include the Monoamine Oxidase Inhibitors (which slow the destruction of these neurotransmitters) and the tricyclic antidepressants; these compounds, which are used in treating diseases like depression; also relatively non-specific—producing many chemical effects besides increasing synaptic dopamine and norepinephrine levels—and thus have a range of unwanted side-effects such as the dangerous increases in blood pressure that occur when people receiving monoamine oxidase inhibitors eat certain foods.

Prior attempts to increase or decrease the levels of dopamine or norepinephrine by modifying neuronal tyrosine levels had been deemed unsuccessful because the total amounts of these compounds in brains and tissues were not noted to change. It was first observed in Wurtman et al. (Science 185:183–184, July 12, 1974) that increases in brain DOPA concentrations, which, under the conditions of the experiments, varied in proportion to the rates at which dopamine and norepinephrine were being synthesized could be obtained by increasing brain tyrosine concentrations, and that decreases in brain DOPA concentrations could be produced by giving rats treatments that decreased brain tyrosine. An example of a treatment that increased brain tyrosine was the administration of tyrosine itself; and example of a treatment that decreased brain tyrosine was the administration of one of the other neutral amino acids, e.g., leucine, that competes with plasma tyrosine for uptake into the brain. Prior to that disclosure, it had been believed that the rate-limiting enzyme, tyrosine hydroxylase, was so saturated with tyrosine, that increases or decreases in brain tyrosine levels would not affect tyrosine's conversion to DOPA. In neither the above Wurtman et al. article nor a subsequent paper by Gibson and Wurtman (Biochem. Pharmacology, 26:1137–1142, June, 1977) was it actually shown that such changes in DOPA accumulation were accompanied by changes in brain dopamine nor norepinephrine levels. Furthermore, in neither was it shown that changing brain tyrosine levels had any effect on the amounts of dopamine nor norepinephrine released into synapses. In my prior filed application Ser. No. 898,740, filed Apr. 24, 1978, it was shown that the administration of tyrosine results in an increase of dopamine or norepinephrine in synapses.

Serum levels of prolactin, a pituitary hormone, are often elevated in animals and humans treated with drugs that block the release of dopamine from nerve terminals, block the formation of dopamine in nerve terminals, or block the ability of dopamine, once released by nerve terminals, to stimulate receptors for this transmitter on other cells. Such increases in blood prolactin levels appear to be undesirable, since several reports indicate that high serum titres of this hormone can predispose to the development of hormone-sensitive carcinomas. Prolactin levels are also pathologically elevated in diseases like spontaneous impotence and idiopathic galactorrhea, or in the presence of tiny pituitary tumors in which patients have not received prolactin elevating drugs.

SUMMARY OF THE INVENTION

The present invention provides a method and composition for reducing blood serum prolactin levels. The tyrosine or its precursor, phenylalanine, can be administered alone, with other amino acids, or in admixture with a drug, in order to lower blood serum prolactin levels as well as to raise dopamine (or norepinephrine) levels. By varying the proportion of tryptophan, another amino acid, in the mixture, the synthesis and synaptic release of serotonin, another brain neurotransmitter, can similarly be controlled. Increased introsynaptic dopamine levels are obtained after tyrosine and/or phenylalanine administration only when the dopamine-releasing neurons are active, i.e., are firing frequently. This happens in the necessary dopamine neurons in the presence of elevated prolactin levels. Increased synaptic norepinephrine levels are obtained by giving tyrosine regardless of whether the norepinephrine-releasing neurons are or are not especially active. In either case, blood serum prolactin levels are reduced. Phenylalanine can, in low doses, be used in place of tyrosine.

DETAILED DESCRIPTION OF SPECIFIC EMBODIMENTS

Figure 1:
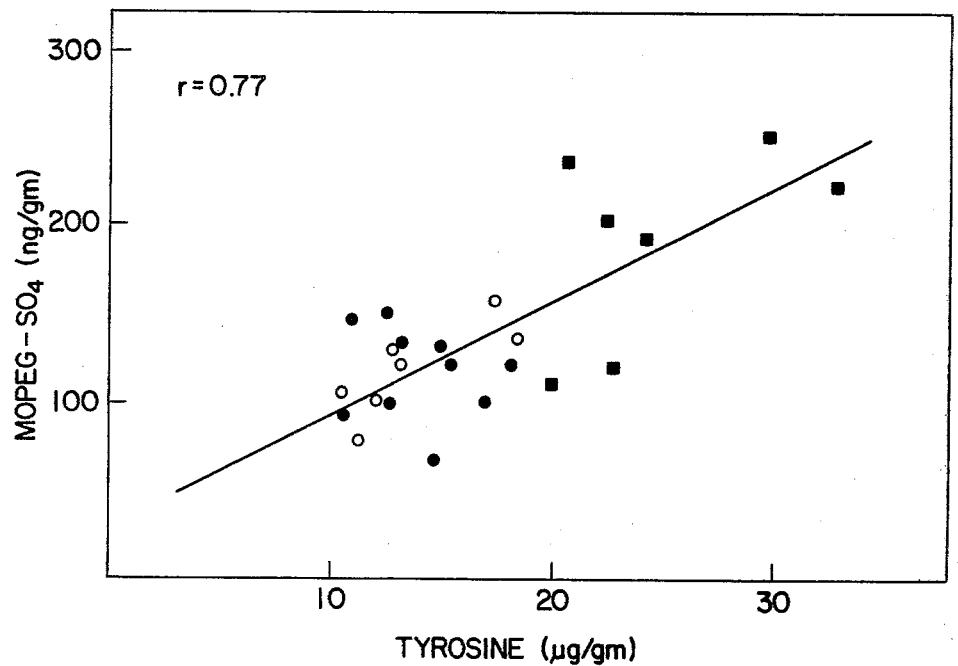

In accordance with this invention, tyrosine and/or phenylalanine is administered to a patient either alone or in combination with one or more drugs which have the undesirable side-effect of increasing blood serum prolactin levels thereby to reduce blood serum prolactin levels. The administration of tyrosine also results in increased levels of dopamine and/or norepinephrine released in synapses. In order to increase dopamine release, it is necessary that the dopamine-releasing neurons in the patient's brain be relatively active, i.e., are firing frequently, such as is the case in patients with Parkinson's Disease. However, release of norepinephrine into synapses is increased whether or not the norepinephrine-releasing neurons are especially active.

The composition of this invention that is utilized to reduce blood serum prolactin levels depends upon the nature of the illness in the patient that is to be treated. When the patient has naturally undesirably high levels of blood serum prolactin, the tyrosine and/or phenylalanine can be administered alone in dosages ranging between about 5 mg/kg and 200 mg/kg, preferably 10 mg/kg and 100 mg/kg body weight. Alternatively, the tyrosine and/or phenylalanine can be administered concomitantly with a drug that is used to treat the patient for an illness and which drug has the undesirable side-effect of raising blood serum prolactin levels. Representative drugs having this undesirable side-effect are reserpine, aldomet, alpha methyl paratyrosine, or clonidine which are administered to reduce blood pressure; haloperidol or pimozide which are administered as tranquilizers; agents like carbidopa that block the peripheral decarboxylation of L-dopa in order to treat Parkinson's Disease; antidepressant agents that modify monoamine metabolism; and estrogen and related compounds that potentiate prolactin secretion. When administered concomitantly with a drug, tyrosine and/or phenylalanine is administered in dosages varying from about 5 mg/kg to 200 mg/kg, preferably between about 10 mg/kg and 100 mg/kg body weight. In some situations, phenylalanine can be used as a substitute for tyrosine, inasmuch as much of this amino acid is converted to tyrosine in the liver, and released into the blood stream for uptake into the brain. However, plasma phenylalanine levels should be less than about double those of tyrosine, since at the higher levels, phenylalanine competes with tyrosine for uptake into the brain, and can inhibit the enzyme tyrosine hydroxylase.

The tyrosine and/or phenylalanine can be administered as free amino acids, esters, salts, natural or synthetic polymers or as constituents of foods. The route of administration can be oral or parental, e.g. intravenous.

The following examples illustrate the present invention and are not intended to limit the same.

EXAMPLE I

This example illustrates that brain norepinephrine can be synthesized by increasing brain tyrosine levels.

This example shows that the rate at which 3-methoxy-4-hydroxy-phenylethyleneglycol-sulfate (MOPEG-SO$_4$), the major brain metabolite of norepinephrine, accumulates in rat brain also varies as a function of brain tyrosine levels. This shows that brain tyrosine levels affect not only the synthesis, but also the turnover and release of brain norepinephrine.

Male Sprague-Dawley rats (Charles River Breeding Laboratories, Wilmington, MA) weighing 150 g were housed in hanging cages (6–8 per cage), given ad libitum access to tap water and a 26% protein diet (Charles River Rat-Mouse-Hamster Maintenance Formula 24RF), and maintained under light (300 microwatts/cm$^2$; Vita-Lite, Duro-Test Corp., North Bergen, N.J.) between 8 AM and 8 PM daily. Rats used for diet experiments were fasted overnight and then allowed to consume the experimental diet starting at 10 AM. Diets of different compositions were prepared in agar gel (35 g/100 ml of water) as described by Gibson et al., Biochem. Pharmacol., 26, 1137–1142 (1977). All amino acids and drugs were injected intraperitoneally.

Norepinephrine synthesis and turnover in brain neurons were estimated by measuring the rate of accumulation of MOPEG-SO$_4$ after probenecid administration or exposure to a cold environment. The MOPEG-SO$_4$ in brain homogenates was isolated using an anion exchange column (A-25 DEAE Sephadex; Pharmacia, Piscataway, N.J.); the method used was basically that of Meek and Neff, Br. J. Pharmacol., 45, 435–441 (1972), but modified to allow both tyrosine and MOPEG-SO$_4$ to be measured in the same sample. An aliquot of each homogenate (in 0.15 M ZnSO$_4$) was first assayed for tyrosine by the method of Waalkes and Undenfriend, J. Lab. Clin. Med., 50, 733–736 (1957). An equal volume of 0.15 M barium hydroxide was then added to the remaining homogenate, which was rehomogenized (Polytron, Brinkman Instruments, N.Y.), centrifuged and assayed for MOPEG-SO$_4$ by the method of Meek and Neff above. Recoveries of MOPEG-SO$_4$ and tyrosine from whole brain homogenates were 70–75% and 85–95%, respectively.

Tyrosine (Grand Island Biological Co., Long Island, N.Y.) and probenecid (Sigma Chemical Co., St. Louis, MO), which are poorly soluble in water, were dissolved in dilute NaOH; the solutions were then buffered to pH 7.4 with hydrochloric acid and brought to a known volume with saline. This yielded a fine suspension that was suitable for injection.

In experiments on stress produced by exposure to cold, animals received the more soluble ethyl-ester form of tyrosine (J. T. Baker, Phillipsburg, N.J.), instead of tyrosine itself, to raise brain tyrosine levels. Data were analyzed by one-way or two-way analysis of variance.

Probenecid treatment significantly raised the MOPEG-SO$_4$ level in brain from 123 ng/g on diluent-injected controls to 175 ng/g in probenecid-treated animals ($P > 0.001$) (Table I). Tyrosine administration alone had no effect on brain MOPEG-SO$_4$; however, pretreatment with this amino acid significantly enhanced the probenecid-induced rise in MOPEG-SO$_4$ (to 203 ng/g, as compared with 175 ng/kg in rats receiving probenecid alone ($P > 0.01$; Table I).

TABLE I

Accumulation of MOPEG-SO$_4$ after Probenecid Administration and Pretreatment with Tyrosine

| Pretreatment | Brain Tyrosine Level (μg/g) | | Brain MOPEG-SO$_4$ Level (ng/g) | |
| --- | --- | --- | --- | --- |
| | Diluent | Probenecid | Diluent | Probenecid |
| Diluent | 13.9 ± 0.5 | 15.7 ± 0.7 | 123 ± 6 | 175 ± 6 |
| Tyrosine | 23.3 ± 1.5 | 24.7 ± 1.3 | 127 ± 2 | 203 ± 8 |

Note:
In each of 3 experiments, groups of 4–6 rats were injected with either a dose of tyrosine (100 mg/kg, i.p.) known to accelerate brain dopa synthesis or its diluent and, 30 min. later, with probenecid (400 mg/kg, 8.p.) or its diluent. Animals were killed 60 min. after the second injection, and their whole brains were analyzed for tyrosine and MOPEG-SO$_4$. Tyrosine administration significantly raised brain tyrosine levels (P ± 0.001, whereas probenecid failed to modify brain tyrosine or its response to exogenous tyrosine. Probenecid significantly raised brain MOPEG-SO$_4$ (P ± 0.001), and tyrosine pretreatment significantly enhanced this response (P ± 0.01). Data were analyzed by two-way analysis of variance. Values are expressed as means ± SEM.

Placing the rats in a cold environment (4° C.) increases norepinephrine turnover; this accelerates the formation of both norepinephrine itself and its metabolite, MOPEG-SO$_4$, in brain neurons. The rats were exposed to cold to determine whether treatments that changed brain tyrosine levels could influence the rate at which the brain accumulates MOPEG-SO$_4$ in rats exposed to cold stress and not given probenecid (FIG. 1).

Exposure to cold for 1 hr. increased brain MOPEG-SO$_4$ levels by about 40% (from 80 μg/g to 114 ng/g; P>0.01). In animals treated with either of the amino acids or with saline, brain tyrosine levels paralleled, and were significantly correlated with those of MOPEG-SO$_4$ (r=77, P>0.05; FIG. 1). Pretreatment with tyrosine raised brain tyrosine levels by about 80% (from 13.3 μg/g, in saline-injected animals, to 24.6 μg/g; P>0.01) and those of MOPEG-SO$_4$ by 70% (from 114 ng/g to 193 ng/g; P>0.01). Pretreatment with valine failed, in this study, to cause significant alterations in brain tyrosine or MOPEG-SO$_4$ levels (14.3 μg/g and 117 μg/g, respectively); however, brain tyrosine and MOPEG-SO$_4$ levels were also significantly correlated in these animals, as in other experimental groups (FIG. 1).

The relationship shown in FIG. 1 was obtained as follows: Groups of rats were injected intraperitoneally with valine (200 mg/kg), an amino acid that competes with tyrosine for uptake into the brain (8), or with tyrosine (125 mg/kg of the ethyl ester) or saline; 30 min. later they were placed in single cages in a cold (4° C.) environment. After 1 hr., all animals were killed, and their whole brains were analyzed for tyrosine and MOPEG-SO$_4$. Control animals were injected with saline and left at room temperature (22° C.), also in a single cages, for 90 min. Each point represents the tyrosine and MOPEG-SO$_4$ levels present in a single brain. Data were pooled from several experiments. Brain tyrosine and MOPEG-SO$_4$ levels in animals kept at room temperature were 14.6 μg/g and 80 ng/g, respectively. In FIG. 1, the symbols are as follows: closed circles, animals pretreated with valine; open circles, animals pretreated with saline; closed squares, animals pretreated with tyrosine.

To determine whether physiologic variations in brain tyrosine level might also influence brain norepinephrine synthesis and turnover (as estimated by measuring MOPEG-SO$_4$ levels), the accumulation of this metabolite in animals exposed to a cold environment was examined after being allowed to consume a single meal that would be likely to elevate tyrosine levels.

Animals that had been fasted overnight were given access to either a protein-free (0% casein) or a 40% casein meal between 10 and 11 AM; they were then placed in the cold (4° C.) for 1 hr., after which they were killed, and their brains analyzed for tyrosine and MOPEG-SO$_4$. Fasted control animals remained at room temperature (22° C.) during this 2-hr. period.

Exposure to cold accelerated the accumulation of MOPEG-SO$_4$ in brains of fasted rats, from 123 ng/g (in fasted control animals kept at 22° C.) to 163 ng/g (P>0.05); this treatment had no effect on brain tyrosine levels (10.1 μg/g vs. 10.5 μg/g). Among animals placed in the cold, consumption of either a 0% or a 40% casein meal enhanced brain MOPEG-SO$_4$ accumulation by 40–50% (Table II; P>0.01). The 0% casein meal increased brain tyrosine by about 40% (P>0.01), whereas the 40% casein meal increased brain tyrosine by 77% (P>0.01).

When the consumption of a protein-free meal failed to elevate brain tyrosine levels, brain MOPEG-SO$_4$ levels also failed to rise (Table II). Among protein-fed animals in this study, the brain tyrosine level increased by about 50% (from 13.4 to 19.5 μg/g, P>0.01), and brain MOPEG-SO$_4$ rose in parallel.

These data show that treatments that increased brain tyrosine levels can accelerate the accumulation of the norepinephrine metabolite MOPEG-SO$_4$ in the brains of rats pretreated with probenecid or exposed to a cold environment. Such treatments can be pharmacologic (i.e., intraperitoneal injection of tyrosine) or physiologic (i.e., consumption of a high-protein meal). They are compatible with the high Km of tyrosine hydroxylase for its substrate, relative to brain tyrosine concentrations. The enzyme is especially vulnerable to substrate limitation when it has been activated, inasmuch as activation selectively enhances its affinity for its cofactor.

MOPEG-SO$_4$ is the major metabolite of norepinephrine formed in rat brain and it is transported out of the brain by a probenecid-sensitive mechanism. After probenecid administration, MOPEG-SO$_4$ accumulates at a linear rate in rat brain for at least 60 min. Since brain norepinephrine levels remain constant during this interval, the rate of MOPEG-SO$_4$ accumulation provides a useful index of the rate of norepinephrine synthesis. This rate apparently is lower in unstressed, probenecid-treated rats than in animals placed in the cold (Tables I and II), however, in both circumstances, it is dependent on brain tyrosine levels.

TABLE II

Brain MOPEG-SO$_4$ Accumulation after Ingestion of a Single Protein-free or 40% Protein Diet among Rats Placed in a Cold Environment

| Treatment | Tyrosine (μg/g) | MOPEG-SO$_4$ (ng/g) |
|---|---|---|
| EXPERIMENT I | | |
| Fasted | 10.5 ± 0.55 | 163 ± 9 |
| Protein-free (0% Casein) | 14.4 ± 0.24* | 239 ± 17* |
| 40% Casein | 18.1 ± 9.85*+ | 228 ± 9*+ |
| EXPERIMENT II | | |
| Fasted | 13.4 ± 0.67 | 195 ± 9 |
| Protein-free (0% Casein) | 13.3 ± 0.81 | 182 ± 18 |
| 40% Casein | 19.5 ± 1.03* | 264 ± 20* |

*Values are significantly different from corresponding fasted group (P < 0.01).
+Values are significantly different from corresponding protein-free group (P < 0.01).
Note:
Groups of 4–6 rats were fasted overnight and then allowed access to one of the test diets at 10 AM. At 11 AM, animals were placed in an environmental chamber at 4° C. for 1 hr. They were killed at noon, and their whole brains were analyzed for tyrosine and MOPEG-SO$_4$. Animals given protein-free and 40% protein diets consumed 9.7 and 10.5 g, respectively, in Experiment I, and 6.2 and 8.0 g in Experiment II. Data presented as means ± SEM.

EXAMPLE II

This example illustrates that brain dopamine release can be enhanced by increasing brain tyrosine levels.

To determine whether tyrosine levels also affect the synaptic release of catechloamine neurotransmitters, the effect of tyrosine administration on the accumulation of the dopamine metabolite, homovanillic acid (HVA) was examined in brains of animals pretreated either with probenecid (a compound that prevents the egress of organic acids from the cerebrospinal fluid, Spector and Lorenzo, 1974) or with haloperidol (a drug that blocks central dopaminergic receptors, Ungerstedt et al, 1969). It was found that increasing the brain tyrosine levels accelerates HVA accumulation in brains of haloperidol-treated animals, but not in animals given probenecid.

Male, 150 to 200 g Sprague-Dawley rats (Charles River Breeding Laboratories, Wilmington, MA) were exposed to light (Vita-Lite, Duro-Test Co., North Bergen, N.J.) between 9 AM and 9 PM daily and allowed access to Big Red Rat Chow (Charles River Breeding Laboratories) and water ad limitum. Drugs were injected intraperitoneally at a volume of 2 ml/kg body weight. Haloperidol was administered as a soluble preparation (Haldol, McNeil Laboratories, La Jolla, CA); tyrosine and probenecid (Sigma Chemical Co., St. Louis, MO) were dissolved in 1 N NaOH and adjusted to pH 10.0. Control animals received the appropriate diluents. Twenty minutes after an injection of tyrosine (100 mg/kg) or its diluent, the animals received haloperidol (2 mg/kg) or probenecid (200 mg/kg); 70 min. later they were killed by decapitation. Brains were quickly removed, and the striata were dissected out (Glowinski and Iverson, 1966), frozen on dry ice, and subsequently assayed for HVA. Tyrosine was assayed in homogenates of the remaining brain (Waalkes and Udenfriend, 1957). To affirm that tyrosine concentration in the homogenates of remaining brain are similar to those in striatum homogenates, brains were compared from groups of 6 animals treated, some of which had received tyrosine and/or haloperidol, and no statistical significance was detected.

Tyrosine hydroxylase activity was measured by a modification of the method of Waymire et al. (1971). Corpora striata were homogenized in 10 volumes of 0.05 M Tris-acetate buffer (pH 6.0), containing 0.2 percent Triton X-100 (Harleco, Philadelphia, PA). The homogenates were centrifuged for 10 min. at 10,000 g, and the supernatant fluids were collected for assay (Coye, 1972). The assay medium contained, in a total volume of 110 $\mu$l: 50 $\mu$l of a supernatant fluid; 65 nmoles of $DMPH_4$ (2-amino-4-hydroxy-6,7-dimethyl-5,6,7,8-tetrahydropteridine hydrochloride [synthetic cofactor obtained from Calbiochem, San Diego, CA]); 29 nanomoles of pyridoxal phosphate; 4 nanomoles of 2-mercaptoethanol; 240 units of catalase; 0.01 millimoles phosphate buffer (pH 6.2); and 10 $\mu$l of aromatic L-amino acid decarboxylase prepared from hog kidneys (Coyle, 1972). Samples were preincubated for 2 min. at 27° C.

The reaction was started by adding 10 $\mu$l of L- 1-$^{14}$C-tyrosine (specific activity, 0.90 $\mu$Ci/mole) to a final concentration of 0.1 mM in the assay medium and then incubating the samxlm at 37° C. for 30 min. The assay was stopped by the addition of 0.5 ml of 10 percent trichloroacetic acid. The acidified medium was then shaken for 2 hours to recover the $^{14}CO_2$, which was trapped by folded filter paper strips placed in 0.2 ml of NCS tissue solubilizer (Amersham/Searle, Arlington Heights, IL). The strips were then transferred to scintillation vials containing 10 ml of Aquasol (New England Nuclear, Boston, MA), and their radioactivity was counted. Blanks utilized either boiled supernatant fluids or complete assay mixtures containing monoiodotyrosine (0.2 mM); both methods yielded similar results.

Figure 2:
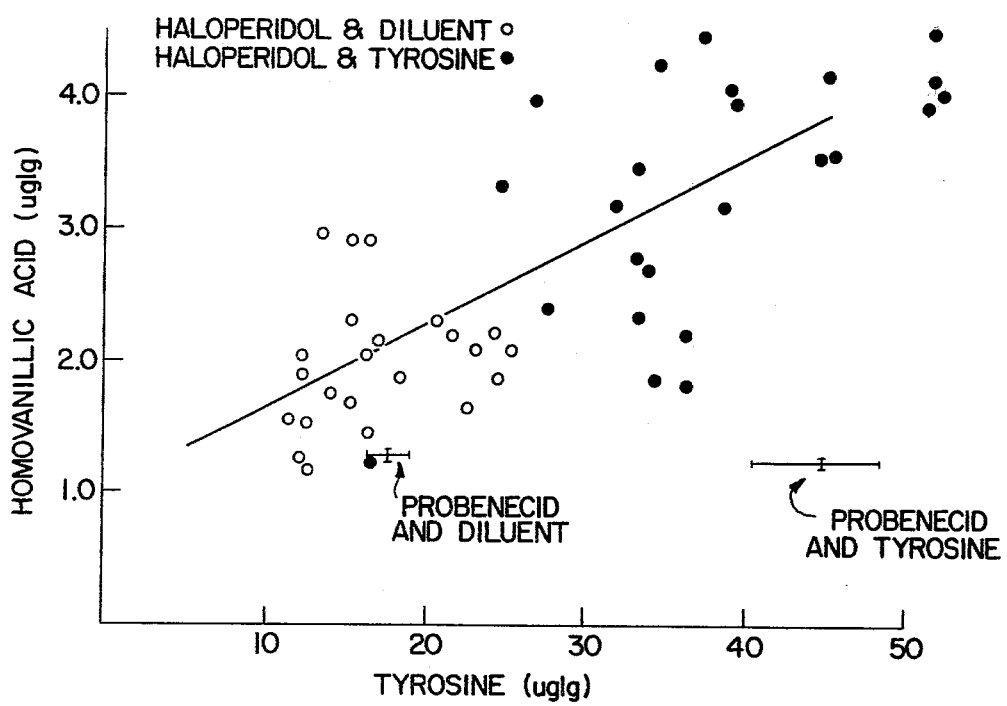

Tyrosine administration markedly potentiated (by 59 percent; $P>0.001$) the accumulation of HVA in striata of haloperidol-treated rats (FIG. 2). It failed, however, to effect the HVA levels in animals given probenecid, even though brain tyrosine levels were elevated to an equivalent extent (FIG. 2). Among haloperidol-treated rats, striatal HVA and brain tyrosine concentrations were highly correlated ($r=0.70$; $P>0.01$) (FIG. 2); no such correlation was observed in probenecid-treated animals.

The failure of HVA accumulation (and thus of dopamine formation) to vary with brain tyrosine level in probenecid-treated rats may reflect the operation of a receptor-mediated feedback mechanism, which couples the activation of striatal dopamine receptors to a suppression of dopamine synthesis. It can be postulated that tyrosine administration initially enhances the synthesis and release of dopamine in striata of probenecid-treated animals, and that the consequent increase in the activation of dopamine receptors causes a feedback decrease in dopamine formation. The decrease in dopamine formation would lead to a fall in the production of HVA. This hypothetical feedback mechanism would fail to operate in haloperidol-treated animals; hence, tyrosine levels could continue to affect dopamine synthesis, even after dopamine release was accelerated.

To examine the possibility that the failure of tyrosine administration to accelerate striatal HVA accumulation in probenecid-treated rats resulted from a feedback change in the kinetic properties of tyrosine hydroxylase, we measured the enzyme's affinity for tyrosine and for its pterin cofactor, $DMPH_4$, on brain samples from each of our experimental groups. The prior administration of tyrosine failed to affect the $K_{m}$ of tyrosine hydroxylase for tyrosine of $DMPH_4$ in vitro (Table I). As noted previously (Zivkovic et al, 1974; Zivkovic and Guidotti, 1974), haloperidol administration did decrease the enzyme's Km for $DMPH_4$ (Table III).

FIG. 2 of tyrosine administration on the accumulation of HVA in corpora striata of rats given haloperidol or probenecid. Rats received tyrosine (100 mg/kg) or its diluent followed in 20 min. by haloperidol (2 mg/kg) or probenecid (200 mg/kg); they were sacrificed 70 min. after the second injection. Data from individual animals receiving haloperidol are indicated by open circles; data from rats receiving haloperidol plus tyrosine are indicated by closed circles. Striatal HVA levels were highly correlated with brain tyrosine levels in all animals receiving haloperidol ($r=0.70$; $P>0.01$). In contrast, the striatal HVA levels of animals receiving probenecid alone ($n=17$) did not differ from those of rats receiving probenecid plus tyrosine ($n=11$). Brain tyrosine and striatal HVA concentrations in each group were (respectively): probenecid, $17.65 \pm 1.33$ and $1.30 \pm 0.10$ $\mu$g/g; probenecid plus tyrosine, $44.06 \pm 3.91$ and $1.31 \pm 0.11$ $\mu$g/g; haloperidol, $17.03 \pm 0.97$ and $2.00 \pm 0.10$ $\mu$g/g; and haloperidol plus tyrosine, $36.02 \pm 2.50$ and $3.19 \pm 0.20$ $\mu$g/g.

TABLE III

Effect of Pretreatment with Tyrosine or its Diluent, Plus Probenecid or Haloperidol, on the Kms of Striatal Tyrosine Hydroxylase for Tyrosine and $DMPH_4$

| Treatment | $K_m$ for tyrosine ($\mu$M) | $K_m$ for $DMPH_4$ (mM) |
|---|---|---|
| Probenecid | $53.9 \pm 2.2$ | $0.72 \pm 0.01$ |
| Probenecid plus tyrosine | $52.1 \pm 1.7$ | $0.67 \pm 0.06$ |
| Haloperidol | $48.1 \pm 1.9$ | $0.13 \pm 0.01$ |
| Haloperidol plus tyrosine | $48.4 \pm 1.1$ | $0.12 \pm 0.01$ |

Animals were treated as described for FIG. 3. Samples of striatum were assayed for tyrosine hydroxylase activity by using tyrosine concentrations of 0.125–1.0 mM and $DMPH_4$ concentrations of 0.1 to 0.5 mM. Haloperidol administration with or without tyrosine significantly reduced the $K_m$ of tyrosine hydroxylase for $DMPH_4$, as compared to that observed in probenecid-treated animals ($P>0.001$, Student's t-test).

These data provide further support for the hypothesis that tyrosine hydroxylase may not always be saturated with its amino acid substrate in vivo—i.e., in animals whose brains are synthesizing larger-than-normal quantities of dopamine as a consequence of dopamine-receptor blockade (by haloperidol). Moreover, they show that increasing the saturation of the enzyme (by administering tyrosine) can enhance not only the formation of dopa and of the catecholamine neurotransmitter, dopamine, but also the release of this transmitter. Control by tyrosine of dopamine synthesis and release can be expected to operate whenever dopaminergic neurons are firing frequently, e.g. in Parkinson's Disease; after haloperidol.

EXAMPLE III

This example illustrates that the administration of tyrosine to animals is useful for reducing blood serum prolactin levels.

Groups of 4 male rats received reserpine (2.5 mg/kg/day, divided into two equal doses each day) intraperitoneally for four days. On day 5, in the morning, no reserpine was administered, but instead half of the animals received tyrosine (200 mg/kg) or the vehicle (saline), and were killed two hours later. Sera were collected and assayed by radioimmunoassay for prolactin. The data are presented below:

| Group | Serum Prolactin |
|---|---|
|  | (ng/ml) |
| Vehicle | 81 ± 11 |
| Tyrosine | 44 ± 2* |

Data are means ± standard errors.
*$P < 0.005$ compared to vehicle levels.

The results show that tyrosine administration lowers serum prolactin levels; thus the amino acid is useful in lowering serum prolactin when these levels are high in human subjects. This form of treatment would be more desirable than the use of dopa, inasmuch as this amino acid produces many side-effects when administered, owing to its conversion to dopamine in all cells in the body. Tyrosine is converted to dopamine only in those cells in the body and brain that normally form the tramsmitter, and thus should be without significant side-effects.

I claim:

1. The process for reducing blood serum prolactin levels in a patient having a condition that results in undesirably high blood serum prolactin levels which comprises administering to said patient an amino acid composition containing between about 5 and 200 mg/kg body weight of tyrosine, phenylalanine or mixtures of tyrosine and phenylalanine.

2. The process of claim 1 wherein said amino acid composition is tyrosine.

3. The process of claim 1 wherein said amino acid composition is phenylalanine.

4. The process of claim 1 wherein said amino acid composition is a mixture of tyrosine and phenylalanine.

* * * * *